US006613562B2

(12) United States Patent
Dvorak

(10) Patent No.: US 6,613,562 B2
(45) Date of Patent: Sep. 2, 2003

(54) METHOD AND APPARATUS FOR SOLIDS PROCESSING

(75) Inventor: Stephen W. Dvorak, Chilton, WI (US)

(73) Assignee: GHD, Inc., Chilton, WI (US)

( * ) Notice: Subject to any disclaimer, the term of this patent is extended or adjusted under 35 U.S.C. 154(b) by 0 days.

(21) Appl. No.: 10/217,602

(22) Filed: Aug. 13, 2002

(65) Prior Publication Data

US 2002/0197665 A1 Dec. 26, 2002

Related U.S. Application Data

(62) Division of application No. 09/534,116, filed on Mar. 23, 2000, now Pat. No. 6,451,589.
(60) Provisional application No. 60/161,246, filed on Oct. 25, 1999.

(51) Int. Cl.[7] .............................................. C12M 1/00
(52) U.S. Cl. ................... 435/290.4; 210/603; 48/127.3
(58) Field of Search ......................... 435/290.1–290.4; 210/603, 605; 48/127.3

(56) References Cited

U.S. PATENT DOCUMENTS

| 3,845,939 A |   | 11/1974 | Waldenville |            |
|-------------|---|---------|-------------|------------|
| 4,057,401 A | * | 11/1977 | Boblitz     | 48/111     |
| 4,100,023 A |   | 7/1978  | McDonald    |            |
| 4,209,303 A | * | 6/1980  | Ricks       | 48/111     |
| 4,230,580 A | * | 10/1980 | Dodson      | 210/170    |
| 4,252,901 A | * | 2/1981  | Fischer et al. | 435/167  |
| 4,274,838 A |   | 6/1981  | Dale et al. |            |
| 4,436,817 A |   | 3/1984  | Nemetz      |            |
| 4,750,454 A | * | 6/1988  | Santina et al. | 123/3    |
| 4,798,802 A |   | 1/1989  | Ryan        |            |
| 5,453,376 A |   | 9/1995  | Ek          |            |
| 5,496,730 A |   | 3/1996  | Teramachi   |            |
| 5,587,320 A |   | 12/1996 | Shindo et al. |          |
| 5,593,590 A | * | 1/1997  | Steyskal    | 210/603    |
| 5,710,042 A |   | 1/1998  | Shindo et al. |          |

OTHER PUBLICATIONS

Unicom Distributed Energy, The Next Generation of Power brochure, 2 pgs.

* cited by examiner

*Primary Examiner*—David A. Redding
(74) *Attorney, Agent, or Firm*—Michael Best & Friedrich LLP

(57) ABSTRACT

This invention provides a waste-processing system capable of processing high-solids wastes such as manure. This invention provides a compact U-shaped digester that allows for recycling of activated sludge to improve the efficiency of the process. Efficiency is also improved through a sludge heating design that creates a current in the digester and efficiently heats the sludge. A composter is provided to further process the sludge through aerobic digestion to create usable fertilizer. Finally, one embodiment provides a turbine that is fueled by biological gases from the digester to generate heat and electricity to be used by the system.

2 Claims, 8 Drawing Sheets

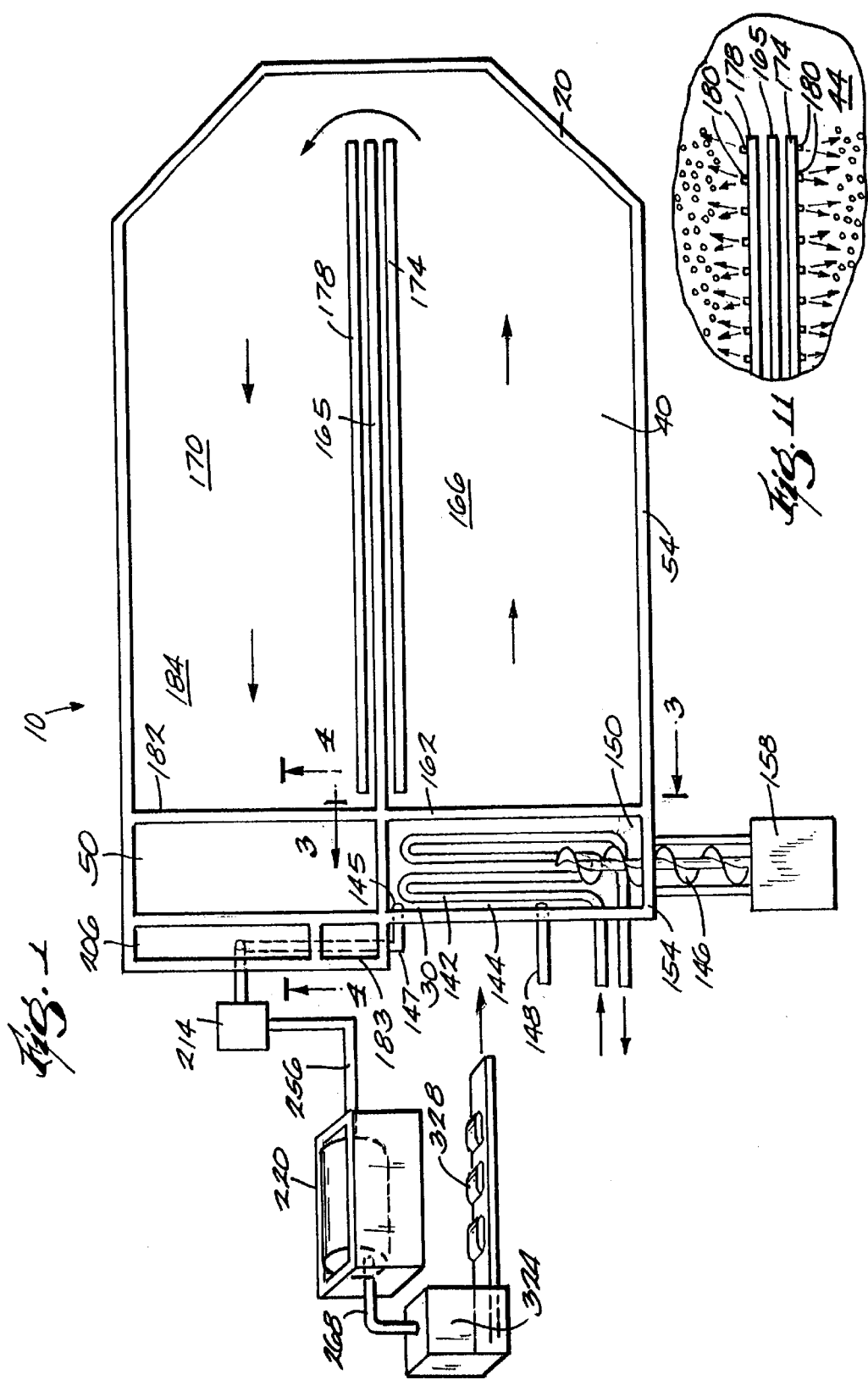

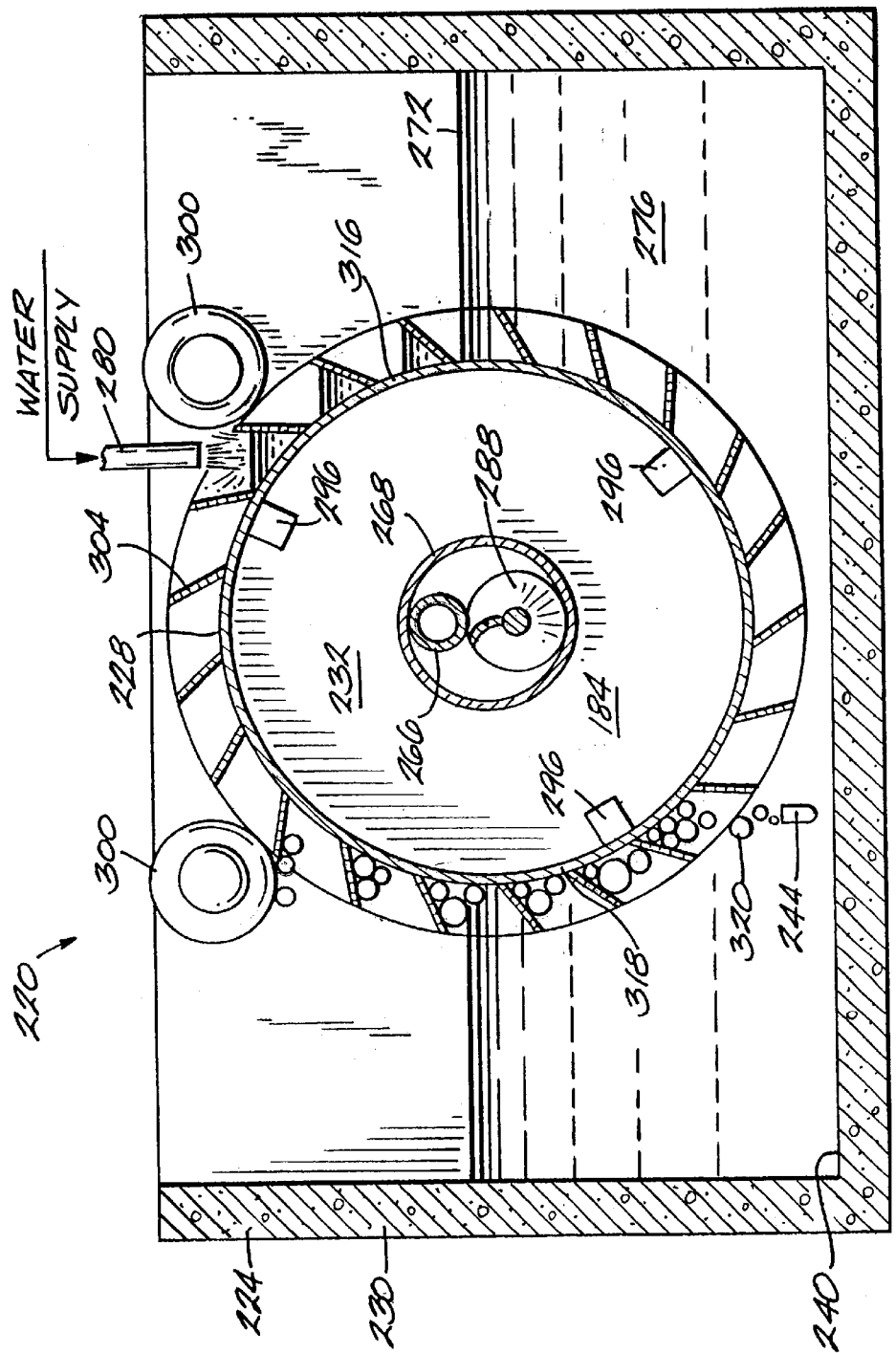

METHOD AND APPARATUS FOR SOLIDS PROCESSING

RELATED APPLICATIONS

This application is a divisional of application Ser. No. 09/534,116 fled on Mar. 23, 2000, which issued as U.S. Pat. No. 6,451,589 B1 which claims the benefit of Provisional application No. 60/161,246 filed Oct. 25, 1999.

BACKGROUND OF THE INVENTION

1. Field of Invention

The invention relates to waste-processing systems for processing manure.

2. Background Prior Art

Many prior art waste-processing systems are designed for low-solids waste, such as municipal waste, that has a solids content of approximately one percent. High-solids wastes such as manure that have a solids content of approximately twelve percent either clog the system or are insufficiently processed. The processing of high-solids waste has typically been performed using a plug flow process that is characterized by a straight-through system.

Prior art waste-processing systems for either high- or low-solids waste use large amounts of purchased energy in the form of electricity or natural gas to generate heat and run pumps to process the wastes because these systems typically exhibit inefficient heating of the waste as it is processed. In addition, prior art waste-processing systems have the added problem of disposing of the products of their processing. It is anticipated that stricter environmental regulations will limit the amount of waste than can be applied to fields as fertilizer because of the phosphates and nitrogen content of the waste. As fields reach their limits, other fields must be found. As the amount of unfertilized land dwindles, either other outlets for waste must be found, or a disposal method that meets the stricter environmental regulations must be developed and used.

SUMMARY OF THE INVENTION

The apparatus and method embodying this invention provide a waste-processing system capable of processing high-solids wastes such as manure. Total process flows are controlled in substantially-closed systems to minimize end waste products and maximize energy efficiency. The apparatus and method embodying this invention provide a compact U-shaped digester that allows for recycling of activated sludge to improve the efficiency of the process. Efficiency is also improved through a sludge heating design that creates a current in the digester and efficiently heats the sludge. Resource use is optimized to preclude the need to purchase outside energy, and to minimize the outflow of water that is unusable without further processing. For example, sludge is dried using waste heat from the processes, rather than using heat generated with energy from outside sources. Finally, a composter is provided to further process the sludge through aerobic digestion to create usable fertilizer, thus minimizing the output of unusable waste products.

A digester for processing high-solids waste is provided comprising a mixing chamber, a clarifier, and a generally U-shaped digester. The mixing chamber is located adjacent the clarifier such that activated sludge may be recycled to the mixing chamber. A heater is provided in the digester such that thermal agitation of the waste causes controlled mixing of wastes in the digester.

In another embodiment, gas jets are provided in the digester such that agitation of the waste by the gas jets causes the waste to be mixed.

In another embodiment, a gas turbine is provided that is fueled by biological gases produced in the waste-processing system.

In another embodiment, a composting tank mounted in a water tank is provided to aerobically digest the waste.

In another embodiment, the composter is replaced with a solids dryer using waste heat to dry the sludge.

In another embodiment, a combination of a fluidizing bed dryer and an air/air heat exchanger replaces the solids dryer to dry the solids and recapture heat produced by the turbines that would otherwise be lost in the turbine exhaust. The heated air in the fluidizing bed dryer evaporates water carried in the effluent from the solids press. The latent heat of vaporization carried by the moisture in the air leaving the fluidizing bed dryer is substantially recaptured in the water condenser.

Other features and advantages of the invention are set forth in the following drawings, detailed description and claims.

BRIEF DESCRIPTION OF THE DRAWINGS

FIG. 1 is a schematic view of a waste-processing system embodying the invention.

FIG. 6 is a cross-sectional view of the composter taken along the 6—6 line in FIG. 5.

FIG. 11 is an enlarged view of a portion of the waste processing system shown in FIG. 1.

Figure 5:
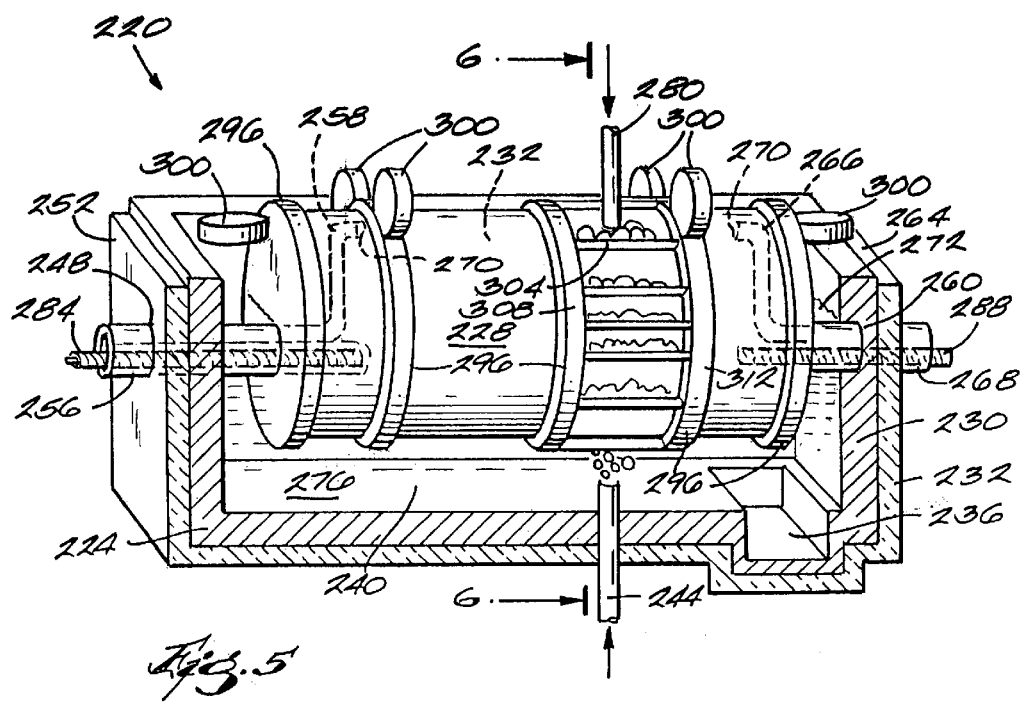
FIG. 5 is a perspective view of a composter of the waste-processing system shown in FIG. 1.

Before one embodiment of the invention is explained in detail, it is to be understood that the invention is not limited in its application to the details of construction and the arrangements of the components set forth in the following description or illustrated in the drawings. The invention is capable of other embodiments and of being practiced or being carried out in various ways. Also, it is understood that the phraseology and terminology used herein is for the purpose of description and should not be regarded as limiting. The use of "including" and "comprising" and variations thereof herein is meant to encompass the items listed thereafter and equivalents thereof as well as additional items.

DETAILED DESCRIPTION OF THE PREFERRED EMBODIMENTS

A waste-processing system 10 embodying the invention is illustrated in FIGS. 1–10. FIGS. 1–6 show the apparatus in which the process is conducted. The system 10 is described in terms of processing manure, but may also be used to process wood pulp, municipal wastes, or organic waste products in general.

FIG. 1 shows schematically the apparatus used to process high-solids farm waste. A digester enclosure 20 includes three major sections: a mixing chamber 30, a digester 40, and a clarifier 50. The digester enclosure 20 is arranged such that a relatively large digester 40 may be built in relatively small space.

Figure 2:
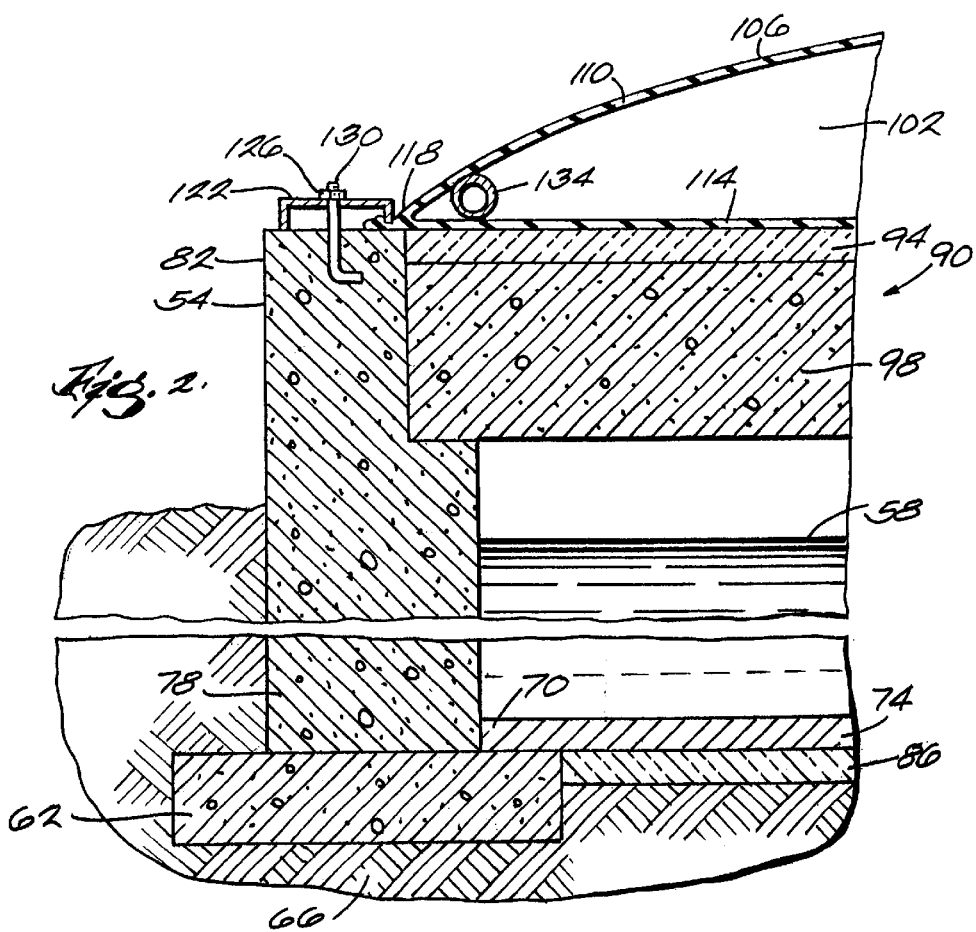
FIG. 2 is a partial cross-section elevational view of the digester of the waste-processing system shown in FIG. 1.

FIG. 2 illustrates the construction of an outside wall 54 of the digester enclosure 20. The height of the outer wall 54 of the digester enclosure 20 is approximately 17 feet, with a liquid depth 58 in the digester enclosure 20 of approximately 14 feet. A footing 62 provides an interface between the wall 54 and the ground 66, and supports the wall 54 and the edge 70 of the floor 74. Both the footing 62 and the wall 54 are constructed of poured concrete. The wall 54 is approximately twelve inches thick at the lower end 78 of the wall 54, and approximately eight inches thick at the upper end 82 of the wall. The floor 74 of the digester enclosure 20 is approximately four inches of concrete. Insulation 86 with a thickness of approximately four inches is arranged below the floor 74 and provides an interface between the floor 74 and the ground 66.

The roof 90 of the digester enclosure 20 is located approximately 15 feet, 8 inches above the floor 74 of the digester enclosure 20. The roof 90 is constructed of an approximately ten-inch thickness 98 of SPANCRETE concrete topped by a four-inch thickness of insulation 94.

A bio gas storage chamber 102 is located above the roof 90. The primary component of the chamber 102 is a liner 106 including an upper liner section 110 and a lower liner section 114. The liner 106 is preferably constructed from high-density polyethylene (HDPE), but may be any other suitable material. The liner 106 is sealed around the edges 118 of the liner 106 by capturing the edges 118 beneath six-inch channel iron 122, which is removably attached to the digester enclosure walls 54 using nuts 126 on a plurality of anchor bolts 130 embedded in the digester enclosure wall 54. A ten-inch PVC pipe 134 is inserted around the periphery of the chamber 102 within the liner 106 to assist in maintaining the seal around the periphery of the liner 106. The liner 106 is constructed such that it can flexibly fill with bio gas as the bio gas is produced in the digester 40, and can be emptied of bio gas as is needed. The bio gas storage chamber 102 may be replaced by any other suitable gas storage system including a roofed storage system.

Returning to FIG. 1, the mixing chamber 30 has horizontal dimensions of approximately 36 feet by 15 feet. Arranged within the mixing chamber 30 is approximately 2000 feet of four-inch black heating pipe 142, which is designed to carry hot water to heat sludge 144 within the mixing chamber 30. An influent pipe 148 carries manure 336 into the mixing chamber 30. Mixing within the mixing chamber 30 is provided by both a mixing nozzle 145 on the end of an activated sludge recirculation pipe 147 and by convective flow resulting from the heating of the manure 336 by the heating pipe 142. A standard auger 146 used for removing solids from the mixing chamber 30 is arranged near the floor 150 of the mixing chamber 30 such that it can transport solids from the floor 150 of the mixing chamber 30 through the wall 154 of the mixing chamber 30 and to a collection device 158. In another embodiment (not shown), solids may be removed from the mixing chamber 30 by any other suitable system, such as a sump pump.

Figure 3:
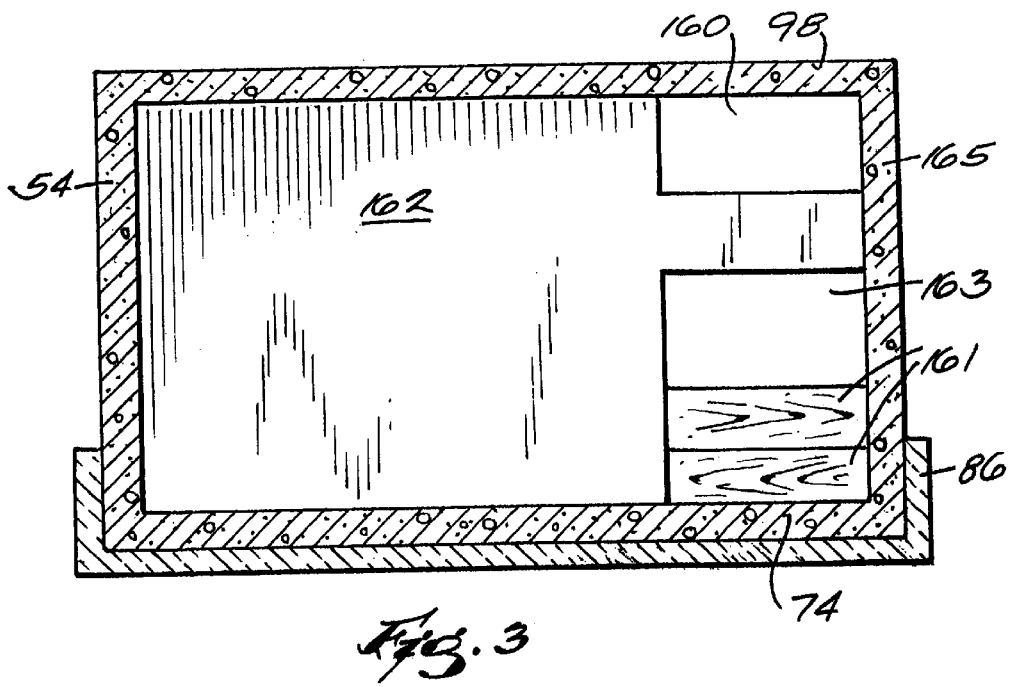
FIG. 3 is a cross-section elevational view of a wall between a mixing chamber and the digester and taken along the 3—3 line of FIG. 1.

As illustrated in FIG. 3, a cutout 160 formed in the wall 162 between the mixing chamber 30 and the digester 40 allows sludge to flow from the mixing chamber 30 into the digester 40. In addition, removable panels 161 are positioned to block opening 163 in the wall 162. Removable panels 161 may be removed as needed to allow greater flow from mixing chamber 30 to digester 40, if desired.

Returning to FIG. 1, the digester 40 is a generally U-shaped tank with overall horizontal dimensions of approximately 100 feet long and 72 feet wide. A center wall 165 approximately 90 feet in length divides the digester 40 into the two legs 166, 170 of the U-shape. Thus each leg 166, 170 of the digester 40 is approximately 100 feet long and 36 feet wide.

The first leg 166 of the digester 40 includes approximately 800 feet of four-inch black heating pipe 174 through which heated water or gas can flow. The heating pipe 174 is arranged along the center wall 165. The second leg 170 of the digester 40 includes approximately 200 feet of four-inch black heating pipe 178, which is also arranged along the center wall 165. In another embodiment illustrated in FIG. 11, the heating pipes 174, 178 may include jet nozzles 180 to dispense heated gas into the sludge 144.

In addition to producing activated sludge 184, the anaerobic digestion of the digester 40 also produces bio gas in the form of methane gas, which is collected in the bio gas storage chamber 102. Any liquid that condenses within the chamber 102 is directed through the effluent pipe 196 (see FIGS. 7–9) to the liquid storage lagoon 198 (see FIGS. 7–9). After a storage time of approximately twelve hours, the collected bio gas is used to fuel an internal combustion engine 138 (see FIG. 7) that, in combination with an electric generator, is used to produce electricity that is sold to a power utility 332 (see FIG. 7). The cooling system of the internal combustion engine 138 also produces hot coolant that is used for heating in the mixing chamber 30 and for heating and agitation in the digester 40. Hot water from the engine 138 passes through an air/water cooler 334 (see FIG. 7) to reduce the temperature of the water from the approximately 180° F. temperature at the exit of the engine 138 to approximately 160° F. for use in the mixing chamber 30 and the digester 40.

Figure 4:
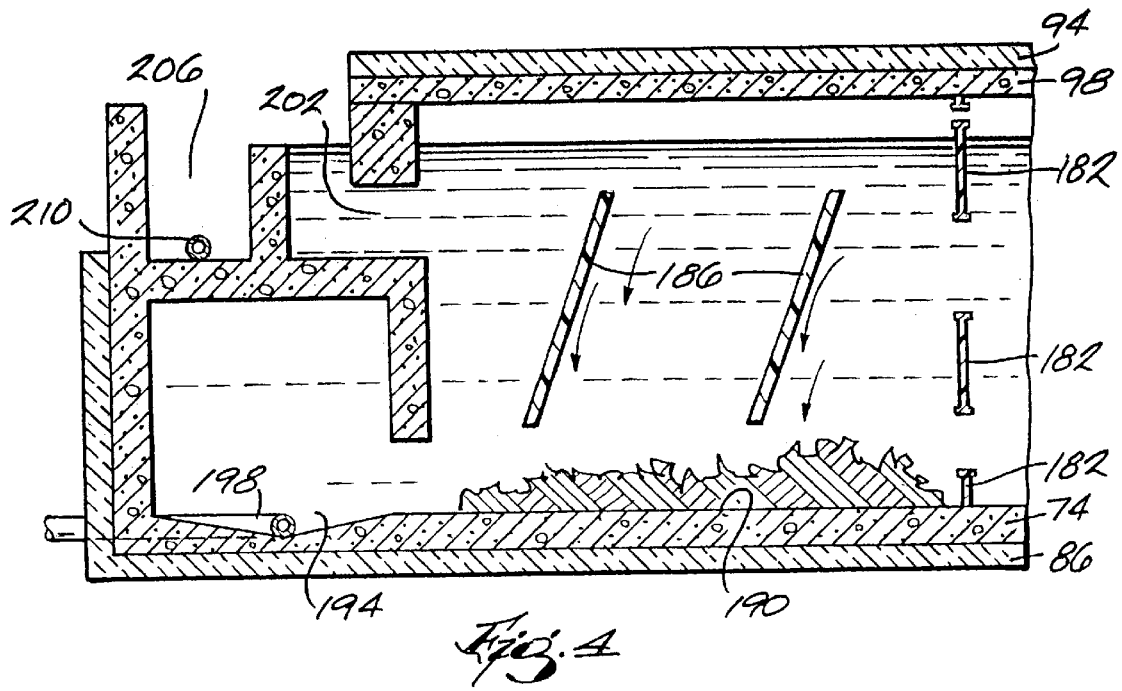
FIG. 4 is a partial cross-section elevational view of a clarifier, taken along the 4—4 line of FIG. 1.

As shown in FIG. 1, the clarifier 50 is located adjacent the digester 40 beyond clarifier panels 182 and adjacent the mixing chamber 30. The clarifier 50 has horizontal dimensions of approximately 36 feet by 21 feet, and is largely empty of any equipment or hardware, with the exception of an equipment room 183. Turning to FIG. 4, the clarifier panels 182 are constructed from HDPE and form a partial barrier between the digester 40 and the clarifier 50. The clarifier panels 182 cover the entire horizontal dimension across the clarifier 50 from center wall 165 to outer wall 54. Separation panels 186 within the clarifier 50 serve to direct solids in a downward direction to the bottom 190 of the clarifier 50, where the solids collect in a sump 194. Sump pipe 198 leads to a standard solids press 214 (see FIGS. 7–9), and to the activated sludge recirculation pipe 147 carrying activated sludge 184 to the mixing chamber 30 (see FIG. 1).

Figure 7:
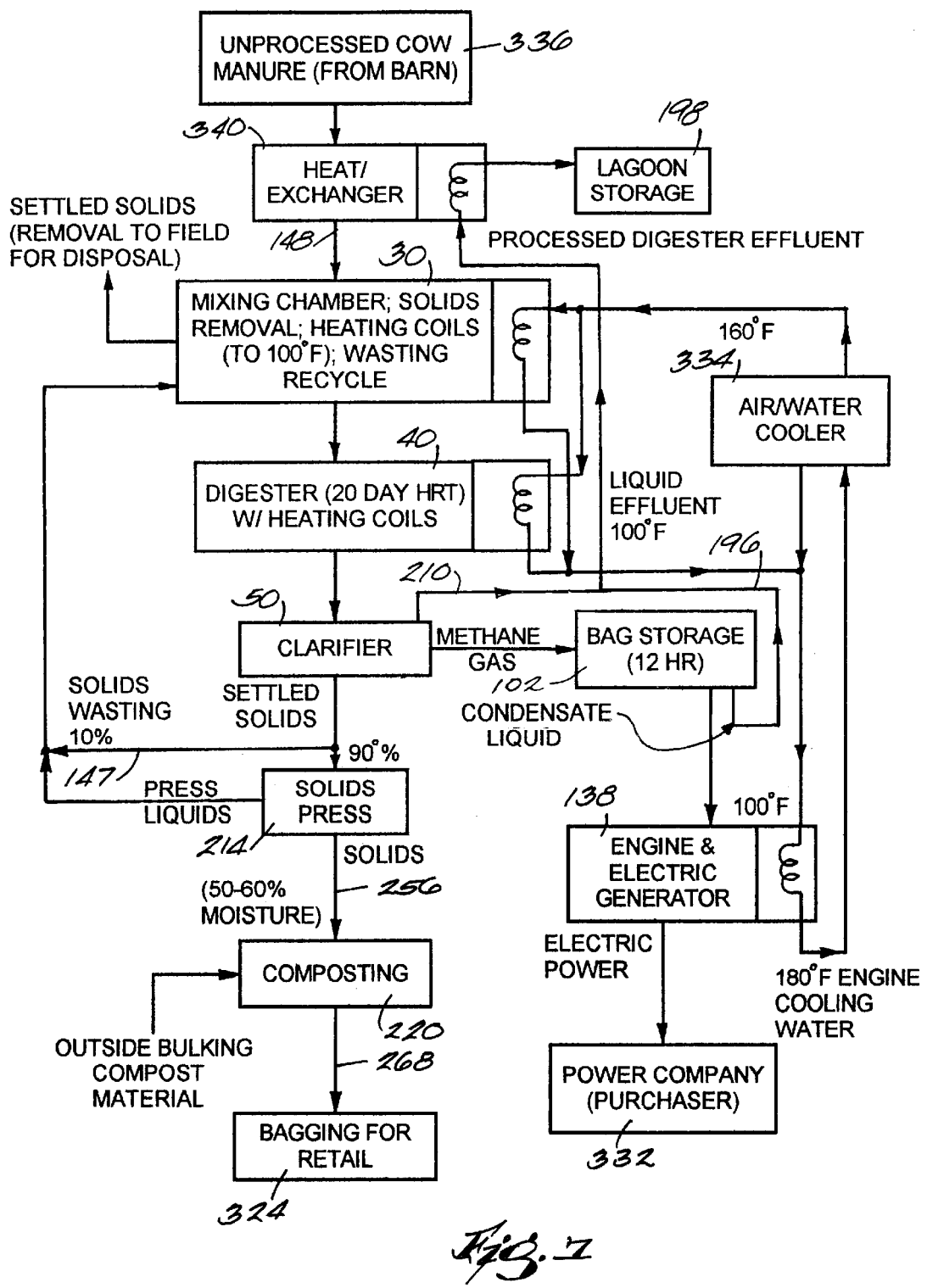
FIG. 7 is a flowchart of the process employed in the waste-processing system shown in FIG. 1.
Figure 8:
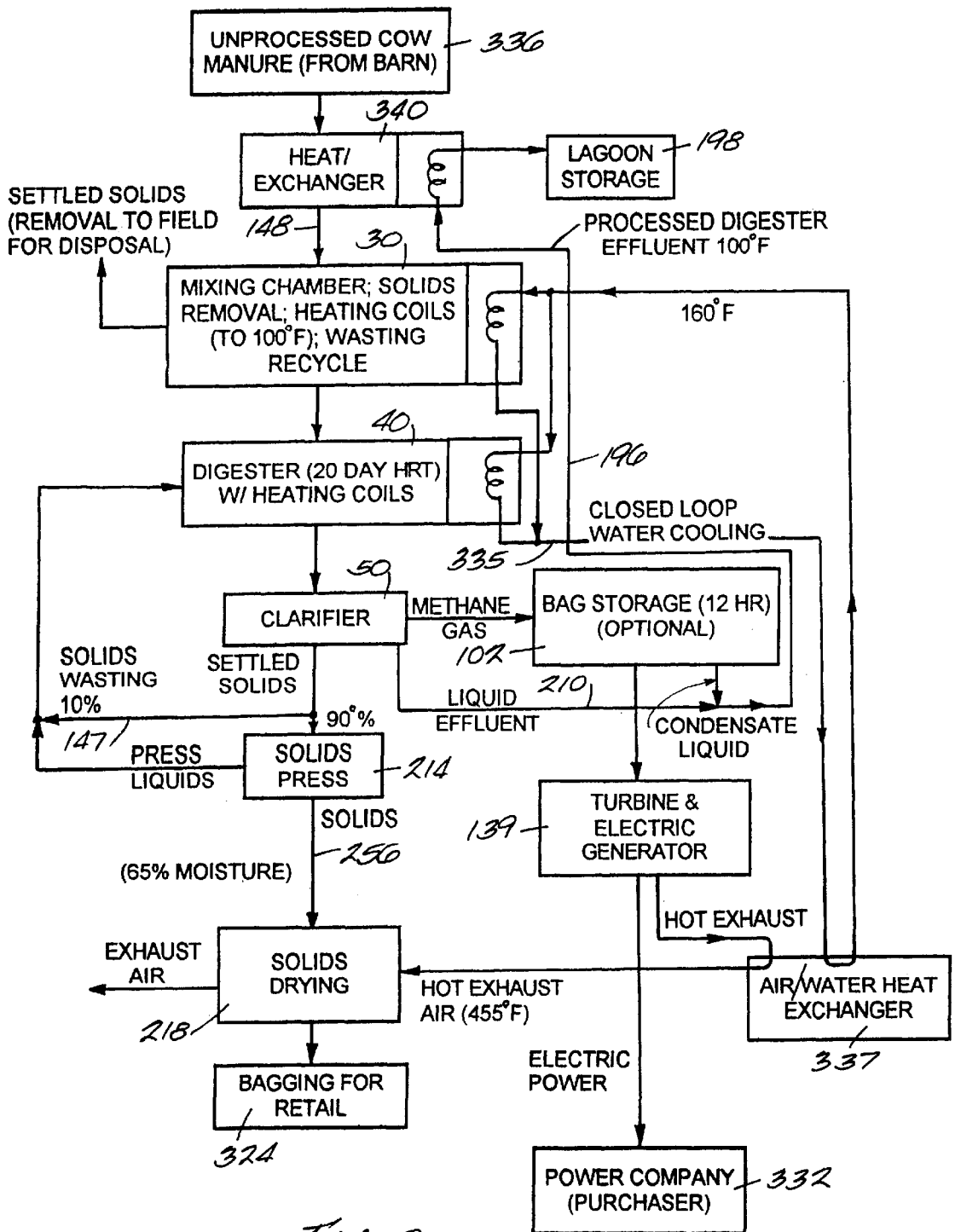
FIG. 8 is a view similar to FIG. 7 and shows an alternative process of the invention.
Figure 9:
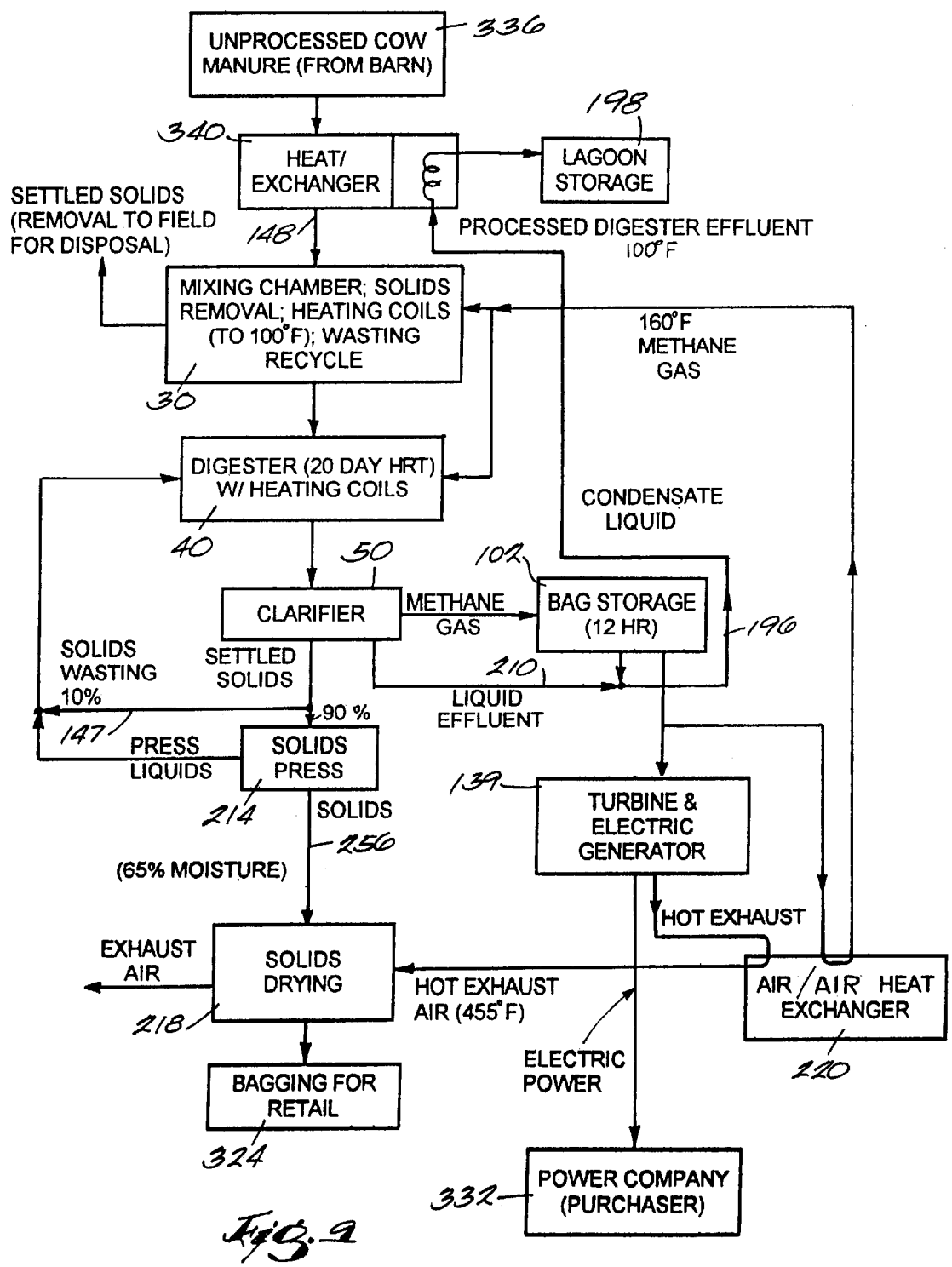
FIG. 9 is a view similar to FIGS. 7 and 8 and shows another alternative process of the invention.

As illustrated in FIGS. 7–9, liquid produced as a result of the operation of the solids press 214 is recycled to the mixing chamber 30 for further processing.

Returning to FIG. 4, liquids in the clarifier 50 decant through gap 202 and collect in a liquid sump 206. A liquid effluent pipe 210 within the liquid sump 206 leads through a heat exchanger 340 (see FIG. 7) and to a liquid storage lagoon 198 (see FIG. 7).

A composter 220 as illustrated in more detail in FIGS. 5 and 6 is located downstream of the solids press 214. The primary components of the composter 220 include a water tank 224 and a composting barrel 228. The water tank 224 is generally a rectangular parallelepiped with six-inch-thick walls 230 constructed from concrete. A four-inch layer of insulation 232 (not shown in FIG. 6) covers the periphery of the walls 230. A sump 236 is located in the floor 240 of the water tank 224. Extending through the floor 240 of the water tank 224 is an air supply pipe 244. A port 248 in the first wall 252 of the water tank 224 accommodates a sludge supply pipe 256 that connects the solids press 214 with the composter barrel 228. A port 260 in the second wall 264 of the water tank 224 accommodates a composter solids exit pipe 268.

The water level 272 of the water tank 224 may be varied to provide buoyant support to the composter barrel 228; the water level 272 as illustrated in FIGS. 5 and 6 is representative of a typical level. The water 276 is typically at 140–160° F. A water inlet pipe 280 provides a flow of water 276 to the composter barrel 228 and the water tank 224. The water 276 is supplied from the cooler 334 of engine 138.

The composter barrel 228 defines an interior chamber 232. A sludge supply auger 284 is located within the sludge supply pipe 256 and extends from within the sludge supply pipe 256 into chamber 232 of the barrel 228. A composted solids exit auger 288 extends from within chamber 232 of barrel 228 into the composter solids exit pipe 268. Each pipe 256, 268 is connected to the ends 292, 294 of the composter barrel 228 using a double rotating union seal with an internal air pressure/water drain (not shown). The pipes 256, 268 and augers 284, 288 are designed such that air that is necessary for drying the sludge and for aerobic digestion may pass through the composter barrel 228. Air passes through solids exit pipe 268 and air inlet pipe 266, into the composter barrel 228, and out through air outlet pipe 258 and sludge supply pipe 256. The air pipes 258, 266 extend vertically to keep their ends 270 above the activated sludge 184 in the composter barrel 228.

The composter barrel 228 is generally cylindrical and approximately 100 feet long and 10 feet in diameter. A plurality of wear bars 296 is attached to the exterior circumference of the barrel 228. Rubber tires 300 acting on the wear bars 296 serve to hold the composter barrel 228 in position.

As illustrated in FIGS. 5 and 6, a plurality of vanes 304 is attached to the barrel 228. These vanes 304 extend between the third and fourth wear bars 308, 312. The vanes 304 are generally parallel to the longitudinal axis of the composter barrel 228. As shown in FIG. 6, to effect cooperation with the vanes 304, the water inlet pipe 280 and the air inlet pipe 244 are laterally offset in opposite directions from the vertical centerline of the composter barrel 228. As a result, when water 276 flows from the water inlet pipe 280, the water 276 collects on the vanes 304 on a first side 316 of the composter barrel 228, and when air 320 flows from the air inlet pipe 244, air 320 collects under the vanes 304 on a second side 318 opposite the first side 316 of the composter barrel 228. The lateral imbalance resulting from weight of water 276 on the first side 316 of the barrel 228 and the buoyancy of the air 320 on the second side of the barrel 228 causes the barrel 228 to rotate in a clockwise direction as viewed in FIG. 6.

The composter barrel 228 is slightly declined toward the exit end 294 of the composter barrel 228 to encourage the activated sludge 184 within the composter barrel 228 to move along the longitudinal axis of the composter barrel 228 toward the exit end 294. As shown in FIG. 6, the composter barrel 228 also includes internal baffles 296 that serve to catch and turn the activated sludge 184 as the composter barrel 228 rotates.

As illustrated in FIG. 1, the composter solids exit pipe 268 connects to a standard bagging device 324 that places the composted solids into bags 328 for sale.

In operation of the waste-processing system 10, as illustrated in FIGS. 1 and 7, unprocessed cow manure 336 from area farms and other sources is transported to the waste processing site and transferred to a heat exchanger 340 where, if necessary, the manure 336 is thawed using warm water from the clarifier 50 by way of liquid effluent pipe 210.

Manure 336 is then transferred from the heat exchanger 340 to the mixing chamber 30 through influent pipe 148, where the manure 336 is mixed with activated sludge 184 recycled from the clarifier 50 by way of activated sludge recirculation pipe 147 to become sludge 144. The sludge 144 is heated to approximately 105–130° Fahrenheit by directing coolant at approximately 160° F. from the engine cooler 334 through the mixing chamber heating pipes 142. In addition, solids such as grit fall to the bottom of the mixing chamber 30 under the influence of gravity and are removed using the mixing chamber auger 146. The solids are then transferred to a disposal site.

After a stay of approximately one day in the mixing chamber 30, the sludge 144 flows through cutout 160 and opening 163, if not blocked, in the wall 162 and into the digester 40, where anaerobic digestion takes place. The activated sludge 184 added to the manure 336 in the mixing chamber 30 serves to start the anaerobic digestion process.

The apparatus and method described herein employ modified plug flow or slurry flow to move the sludge, unlike the plug flow in prior art systems. The digester heating pipes 174, 178 locally heat the sludge 144 using hot water at approximately 160° F. from the cooler 334 of the engine 138, causing the heated mixed sludge to rise under convective forces. The convection develops a current in the digester 40 that is uncharacteristic of prior art high-solids digesters. Sludge 144 is heated by the digester heating pipes 174, 178 near the digester center wall 165, such that convective forces cause the heated sludge 144 to rise near the center wall 165. At the same time, sludge 144 near the relatively cooler outer wall 54 falls under convective forces. As a result, the convective forces cause the sludge 144 to follow a circular flow path upward along the center wall 165 and downward along the outer wall 54. At the same time, the sludge 144 flows along the first and second legs 166, 170 of the digester 50, resulting in a combined corkscrew-like flow path for the sludge 144.

In another embodiment (not shown), hot gas injection jets using heated gases from the output of the engine 138 replace the hot water digester heating pipes 174, 178 as a heating and current-generating source. The injection of hot gases circulates the sludge 144 through both natural and forced convection. A similar corkscrew-like flow path is developed in the digester 40.

In the arrangement shown in FIG. 1, the U-shape of the digester 40 results in a long sludge flow path and thus a long residence time of approximately twenty days. As the sludge 144 flows through the digester 40, anaerobic digestion processes the sludge 144 into activated sludge 184. The anaerobic digestion process also reduces the phosphate content of the liquid effluent by approximately fifty percent, which is a key factor in meeting future environmental regulations.

From the digester 40 the activated sludge 184 flows into the clarifier 50. The clarifier 50 uses gravity to separate the activated sludge 184 into liquid and solid portions. Under the influence of gravity and separation panels 186, the liquid portion rises to the top of the mixture and is decanted through a gap 202 into a liquid sump 206. It is later transferred to lagoon storage 198 through effluent pipe 210. The liquid is then taken from the lagoon 198 for either treatment or use as fertilizer.

The solid portion of the activated sludge 184 settles to the bottom 190 of the clarifier 50 in sump 194. From there, approximately ten to twenty-five percent of the activated sludge 184 is recycled to the mixing chamber 30 through activated sludge recirculation pipe 147 to mix with the incoming manure 336, as described above. The remaining approximately seventy-five to ninety percent of the activated sludge 184 is removed from the clarifier 50 through sump pipe 198 and is transferred to the solids press 214 in which the moisture content of the activated sludge 184 is reduced to approximately sixty-five percent.

From the solids press 214, the activated sludge 184 is transferred through sludge supply pipe 256 using sludge supply auger 284 to the interior chamber 232 of the composter barrel 228 where the activated sludge 184 is heated and agitated such that aerobic digestion transforms the activated sludge 184 into usable fertilizer. Outside bulking compost material can be added to the chamber 232 to make the fertilizer more suitable for later retail sale. As the composter barrel 228 turns, baffles 296 within the chamber 232 agitate and turn the sludge. This agitation also serves to aerate the sludge to enhance aerobic digestion. At the same time, the tank of water 224 in which the barrel 228 sits heats the barrel 228. This heating also promotes aerobic digestion.

In the preferred embodiment, water 276 falling from the water inlet pipe 280 and air 320 rising from the air inlet pipe 244 collects on the vanes 304 and causes the composter barrel 228 to turn around its longitudinal axis. In other embodiments, direct motor or belt drives, or any other suitable drive mechanism may turn the composter barrel 228.

As the activated sludge 184 turns over and undergoes aerobic digestion in the chamber 232, it also travels longitudinally and eventually exits the composter barrel 228 through the composter solids exit pipe 268, driven by the composter solids exit auger 288. The processed sludge, which has become usable fertilizer at approximately forty-percent moisture, is transferred to a bagging device 324. In the bagging device 324, the processed sludge is bagged for sale as fertilizer.

In an alternative embodiment illustrated in FIG. 8, a turbine 139 replaces the internal combustion engine as described above. The turbine 139 is preferably an Allied-Systems TURBOGENERATOR turbine power system as distributed by Unicom Distributed Energy, but may be any other suitable turbine. The turbine 139 is fueled by the methane collected in the bio gas storage chamber 102. The differences with the use of a turbine 139 from the previously-discussed process are outlined as follows. Instead of an engine cooler 334 producing heated coolant, the turbine 139 produces exhaust gases at approximately 455° F. The hot exhaust gases are used to heat water in a closed loop 335 through an air/water heat exchanger 337. The heated water is then used for heating in the mixing chamber 30 and for heating and agitation in the digester 40. This embodiment is used in conjunction with a composter (not shown) as described above.

As shown in FIG. 8, the composter is replaced with a solids dryer 218 in which hot exhaust from the turbine 139 is used to dry the sludge taken from the solids press 214. From the solids dryer 218, the activated sludge 184 is transferred to a bagging device 324. In the bagging device 324, the processed sludge is bagged for sale as fertilizer.

In another embodiment illustrated in FIG. 9, hot exhaust gases from the turbine 139 are used to heat methane from the bio gas storage chamber 102 to approximately 160° F. in an air/air heat exchanger 220. The heated methane is then injected into the mixing chamber 30 and the digester 40 for heating and agitation. In this embodiment, it is possible to seal off the digester 40 from any air contamination because only methane is used for heating and agitation. The methane is then recaptured in the bio gas storage chamber for reuse. This embodiment is used in conjunction with a composter (not shown) as described above.

In the embodiment illustrated in FIG. 9, the composter is replaced with a solids dryer 218 in which hot exhaust from the turbine 139 is used to dry the sludge taken from the solids press 214. Again, from the solids dryer 218, the activated sludge 184 is transferred to a bagging device 324. In the bagging device 324, the processed sludge is bagged for sale as fertilizer.

Figure 10:
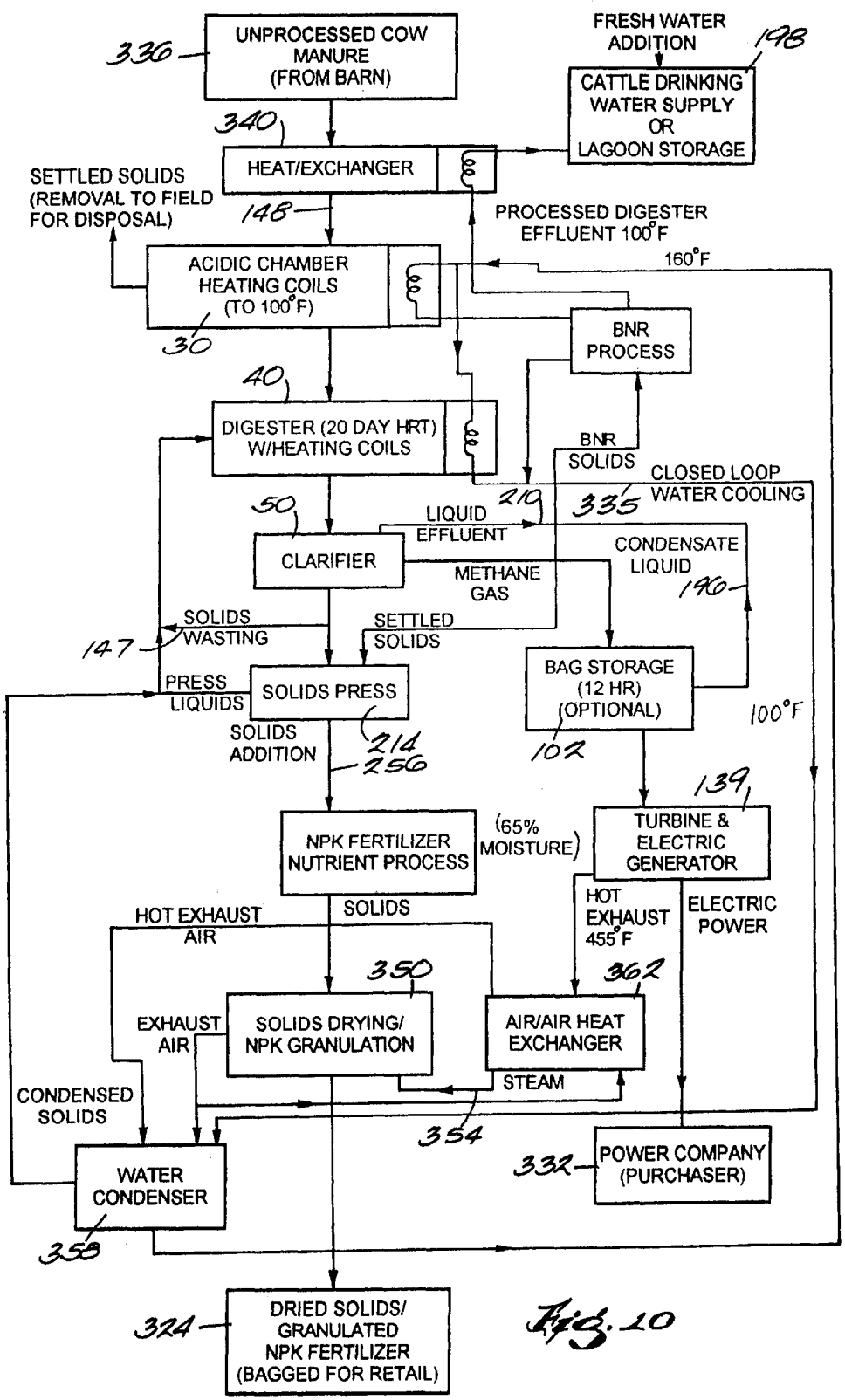
FIG. 10 is a view similar to FIGS. 7–9 and shows another alternative process of the invention.

In still another embodiment illustrated in FIG. 10, a fluidizing bed dryer 350 takes the place of the composter or solids dryer described in previous embodiments. Pressed bio solids at approximately 35 percent solids from the solids press 214 enter the fluidizing bed dryer 350 where the solids are fluidized using heated air in a closed-loop air system 354. This fluidizing results in moisture from the bio solids being entrained in the heated air. The moisture-laden heated air passes through a water condenser 358 where water is removed from the heated air and circulated back to the heating pipe 142 in the mixing chamber 30 and to the heating pipe 174 in the digester 40. Heat is provided to the closed-loop air system 354 through an air/air heat exchanger 362. Hot exhaust gases from a series of turbines 139 provide heat to the air/air heat exchanger 362. The exhaust gases then enter the water condenser 358 to remove combustion moisture from the turbine exhaust before the remaining gases are vented to the atmosphere. The water condenser 358, in addition to recapturing water, also recaptures heat carried by the turbine exhaust and by the heated air in the closed-loop air system 354. This recaptured heat is used to heat the water circulating in the closed-loop water heating system.

The combination of a fluidizing bed dryer 350 and an air/air heat exchanger 362 recaptures heat produced by the turbines 139 that would otherwise be lost in the turbine exhaust. The heated air in the fluidizing bed dryer 350 evaporates water carried in the effluent from the solids press. The latent heat of vaporization carried by the moisture in the air leaving the fluidizing bed dryer 350 is substantially recaptured in the water condenser 358. The closed-loop air system 354 allows for air with reduced oxygen content to be used in the fluidizing bed dryer 350 to reduce the risk of fire associated with drying organic material. In addition, the closed-loop air system 354 allows for the addition of an auxiliary burner (not shown) if needed to process wetter material in the fluidizing bed dryer 350. A variable speed fan (not shown) can be added to the closed-loop air system 354 after the water condenser 358 to pressurize the air for the fluidizing bed dryer 350.

In the embodiment illustrated in FIG. 10, from the solids dryer 218, the activated sludge 184 is transferred to the bagging device 324. In the bagging device 324, the processed sludge is bagged for sale as fertilizer.

In another embodiment (not shown), the composter is replaced with a solids dryer 218 in which hot exhaust from the internal combustion engine 138 is used to dry the sludge taken from the solids press 214. Again, from the solids dryer 218, the activated sludge 184 is transferred to a bagging device 324. In the bagging device 324, the processed sludge is bagged for sale as fertilizer.

Various features of the invention are set forth in the following claims.

What is claimed is:

1. A system for processing high solids waste material, the system comprising:

a digester for anaerobically digesting the waste material, the digester producing methane and including a closed container for holding high solids waste material, the closed container including a first passage in which the waste material flows in a first direction, the first passage having first and second ends, the first end including an inlet for waste material, and a second passage in which the waste material flows in a direction opposite the first direction, the second passage having first and second ends, the second end including an outlet, the first passage being separated from the second passage by a divider, the second end of the first passage being adjacent the first end of the second passage, and the first end of the first passage being adjacent the second end of the second passage; and a composter for aerobically digesting waste material, wherein the composter is connected to the outlet and receives waste material from the digester through the outlet, the composter including a container and an air inlet.

2. The system of claim 1, further comprising a turbine producing heated exhaust, the turbine being fueled by methane gas produced in the digester, and having an exhaust outlet for discharging heated exhaust; and the exhaust outlet being connected to the digester to heat waste in the digester.

* * * * *